United States Patent [19]
Spencer

[11] Patent Number: 6,010,483
[45] Date of Patent: Jan. 4, 2000

[54] PATIENT CONTROLLED ANALGESIA DEVICE FOR USE WITH ULTRASHORT ACTING OPIOID MEDICATION AND METHOD FOR USING THE SAME

[76] Inventor: Robert F. Spencer, 3 Kent St., Concord, N.H. 03301

[21] Appl. No.: 08/995,140

[22] Filed: Dec. 19, 1997

Related U.S. Application Data

[60] Provisional application No. 60/033,758, Dec. 23, 1996.

[51] Int. Cl.$^7$ .................................................. A61M 1/00
[52] U.S. Cl. .................................................. 604/151
[58] Field of Search ................................. 604/131, 151; 128/DIG. 13, DIG. 12

[56] References Cited

U.S. PATENT DOCUMENTS

| | | | |
|---|---|---|---|
| 4,828,551 | 5/1989 | Gertler et al. | 604/208 |
| 5,069,668 | 12/1991 | Boydman | 604/121 |
| 5,207,645 | 5/1993 | Ross et al. | 604/141 |

FOREIGN PATENT DOCUMENTS

| | | | |
|---|---|---|---|
| 0079405 | 5/1983 | European Pat. Off. | 604/151 |
| 8502546 | 6/1985 | WIPO | 604/131 |

*Primary Examiner*—Jeffrey A. Smith
*Attorney, Agent, or Firm*—George H. Spencer

[57] ABSTRACT

A pump or method supplying patient controlled analgesia to a patient. The infusion flow rate of the analgesic is increased in response to a command given by the patient receiving the analgesic, and a lock out interval is provided during which time the actuation of the pump by the patient produces no further incremental increase in the flow rate of the analgesic.

8 Claims, 4 Drawing Sheets

PATENT CONTROLLED ANALGESIA DEVICE FOR USE WITH ULTRASHORT ACTING OPIOID MEDICATION AND METHOD FOR USING THE SAME

CROSS-REFERENCE TO RELATED APPLICATION

This applications claims the benefit of Provisional Application 60/033,758 Dec. 23, 1996.

BACKGROUND OF THE INVENTION

The present invention relates to a patient controlled analgesia device for use with ultrashort acting opioid medication and a method for using the same.

Patient controlled analgesia (PCA) is a technique for providing pain relieving medicine to patients. Most commonly, it refers to intravenous, epidural, or subcutaneous administration of a liquid opioid via a pumping device with the patient having some ability to control the timing and quantity of drug delivery. Pumps currently in use for PCA generally give the clinician two parameters to set when prescribing a given drug for a patient. These include (1) a dose or bolus amount of drug administered whenever the patient presses a button and (2) a lockout interval which determines how soon after a bolus is administered a second bolus will be delivered if the patient presses the button again. If a patient presses the button before the lockout interval has elapsed, the PCA pump simply ignores the "request." The dose and lockout are programmed into the pump for an individual patient and drug combination. The dose is prescribed based on the clinician's assessment of the patient's opioid requirement (depending on weight, habituation, or other factors). The lockout interval is generally set depending on the time to onset of clinical effect of a given drug. The lockout interval is used to prevent a patient from giving himself or herself another bolus before the previous bolus has had a chance to take effect.

Sometimes a third parameter is programmed into a pump providing PCA. This is the flow rate of a continuous infusion of medication providing a background of opioid on top of which PCA is added. The continuous infusion is adjusted to provide the minimum amount of drug needed by a patient over time. The PCA component then allows the patient to administer extra (rescue or break-through-pain) doses as needed. This technique of using a continuous infusion along with PCA minimizes the requirement for a patient to push the button repeatedly as a bolus wears off. This is particularly useful at night when the patient's sleep would otherwise be interrupted regularly. Of note is the fact that currently used pumps do not generally allow the patient to adjust the rate of a continuous infusion. When they do, the patient must go through a series of programming inputs just like the clinician would when programming the pump initially.

PCA opioid administration, as described above has an inherent safety feature which prevents over dosage if the dose and lockout interval are set appropriately. Opioids have a side-effect of sedation. Therefore, if patients give themselves too much drug, they become sleepy and cease pressing the button. However, a supplemental continuous infusion, if set too high, can overcome this safety feature by providing more opioid to a sedated or even unconscious patient. This is why currently used pumps do not generally allow the patient to increase the rate of a continuous infusion.

The current method of providing patient controlled analgesia relies on the fact that boluses of commonly used opioids have a relatively long duration of action, i.e., an hour or more. However, the Federal Drug Administration (FDA) recently approved marketing of an opioid, remifentanil hydrochloride (hereinafter "remifentanil")marketed by Glaxo Wellcome, Inc., Research Triangle Park, N.C. 27709, under the trademark "ULTIVA". Remifentanil has a duration of action of only several minutes. Unless a patient's pain is intermittent and very short lived, current PCA pumps are not well suited for use with remifentanil. A patient with continuing pain, using a standard PCA pump to administer boluses of such a short acting opioid, would be required to press the button too often to be practical.

On the other hand, remifentanil or other ultrashort acting opioids can have significant advantages over longer acting opioids when administered by continuous infusion. The response to a change in an infusion flow rate would be very quick. This would be extremely useful when a patient's opioid requirement is not known or when the intensity of a patient's pain changes quickly. Currently, pumps are available which allow a continuous infusion to be adjusted and/or a bolus given. However, currently available pumps are not designed to have their flow rate controlled by a patient with a single push of a button as is possible for bolus PCA administration.

BRIEF DESCRIPTION OF THE INVENTION

The invention described is designed to combine two things: (1) the PCA feature of a single button for a patient to push when more pain medicine is needed and (2) the greater flexibility associated with a continuous infusion of an ultrashort acting opioid. This is accomplished by having the continuous infusion flow rate step up to a higher rate for a given period of time each time the single button is pushed. The clinician can program both the step up amount and the duration of the increased rate as well as the baseline infusion rate and the lock out interval (during which time a button push provides no further incremental increase in flow rate).

Other features are also included for added safety to prevent over dosage. These include: (1) The ability to set a maximum infusion rate above which the pump will not go—even if the clinician set parameters would otherwise allow it. (2) Controls which allow the patient to decrease the baseline infusion rate if early symptoms of opioid toxicity occur. (3) Feedback to the pump regarding sedation or respiratory depression that may indicate profound opioid overdose—triggering discontinuation of the infusion until the patient pushes the button again. If the patient is able to push the button, there has either been a false alarm or adequate recovery. (4) Along with discontinuation of the infusion, the pump is also programmed to provide a loud audible alarm to arouse the patient in the event of an overdose causing sedation or respiratory depression.

Measurable patient parameters which indicate sedation or respiratory depression include: respiratory rate, respiratory depth, hemoglobin oxygen saturation, and patient movement. Various combinations of such parameters may be used to provide both sensitive and specific feedback to the pump regarding possible overdose.

Another useful feature of the pump includes its ability to collect and store data (such as time of day, opioid infusion rates, patient controlled increases or decreases, and physiologic parameters) for later review by the clinician. These data can either be displayed on the pump's screen or transferred to a personal computer via a data-link port. This information may provide important clues regarding the timing and degree of variation in a patient's pain reflected in his or her opioid requirement. Currently available PCA pumps can provide some of this information. However, because the device described above can be programmed to adapt more precisely to changes in a patient's opioid requirement over time, the information obtained with it may be more useful. Once a clearly defined pattern of opioid use has been established, the clinician can more rationally prescribe a patients opioid therapy, either with continued use of PCA remifentanil intravenously or with other appropriate medications and routes of administration.

The device is a self contained pump having an on/off switch, a display screen, a key board, a replaceable battery, a replaceable drug reservoir cassette, a PCA button with plug to connect to pump via socket, a computer output data-link port and related equipment, a physiologic data input port and related equipment, an audible alarm speaker, a replaceable intravenous (IV) tubing, an internal adjustable rate pump, and an internal processor.

DETAILED DESCRIPTION OF THE PREFERRED EMBODIMENTS

Figure 1:
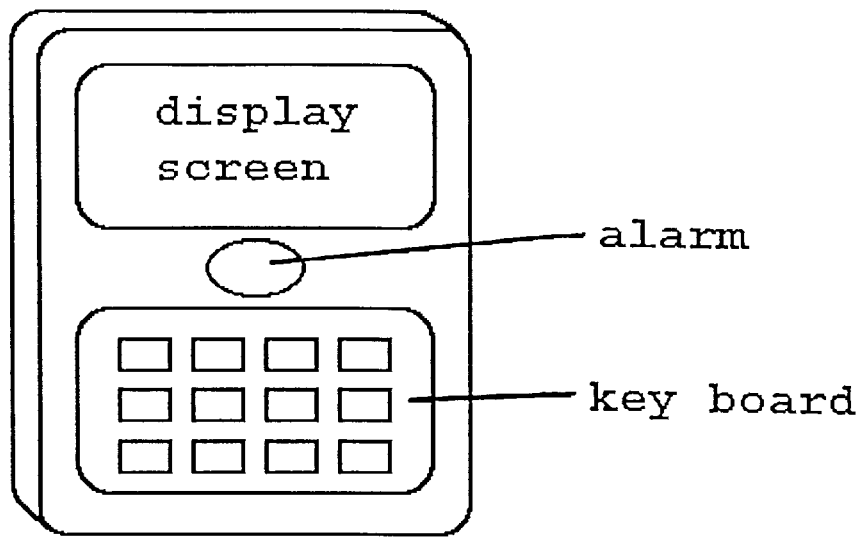
FIGS. 1, 2, 3, and 4 show, respectively, the front, back, left and right sides of the device.
Figure 2:
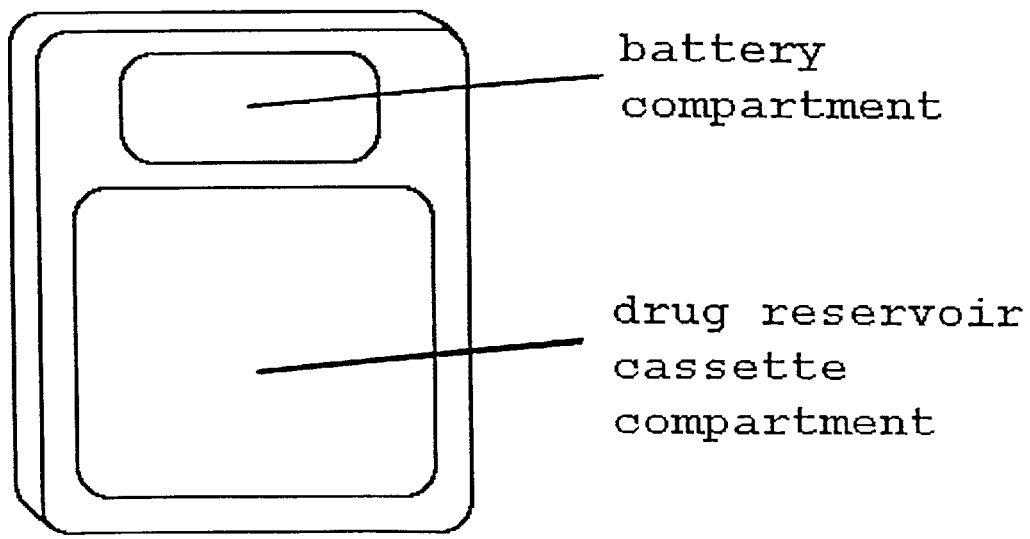
Figure 3:
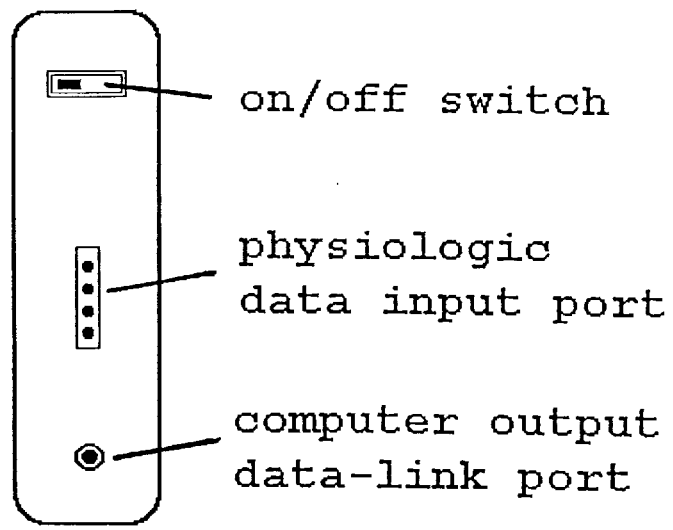
Figure 4:
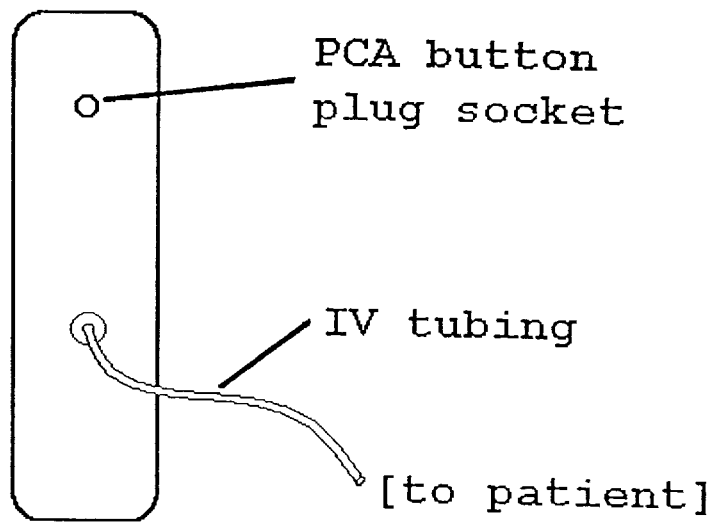
Figure 5:
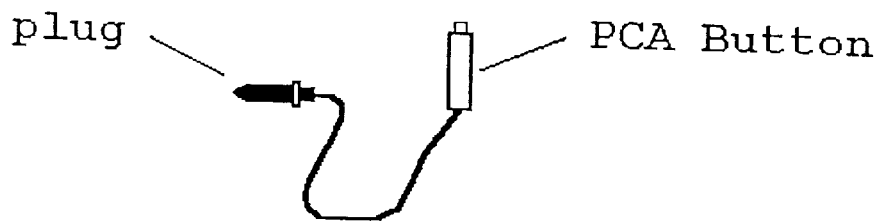
FIG. 5 shows the plug and button unit.
Figure 6:
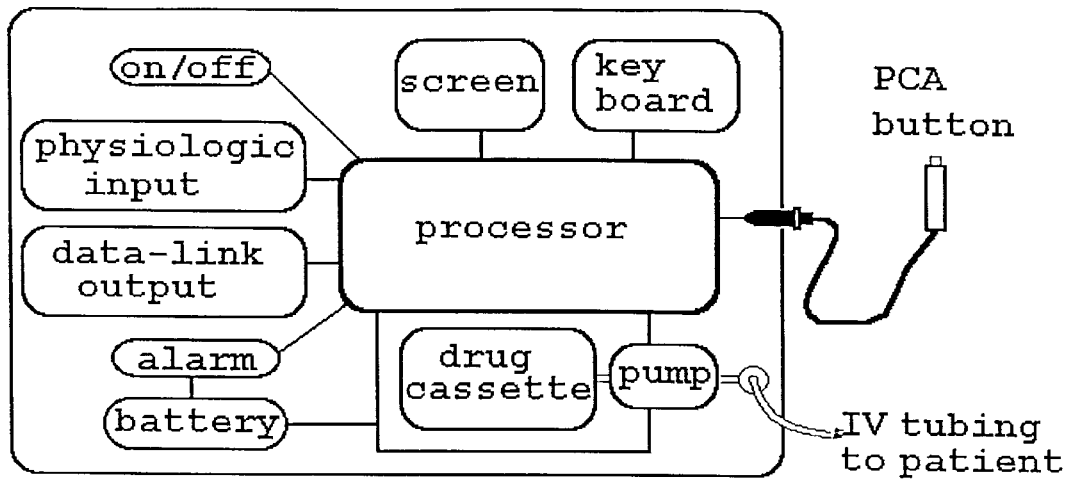
FIG. 6 is a schematic diagram of the internal connections.

The structural features of the pump device as a whole are shown in FIGS. 1–5, the parts being labeled in the drawings for the sake of clarity.

The PCA device with remifentanil, an ultrashort acting opioid, may be used therapeutically and/or diagnostically to assess significant variations in pain levels over time. Parameters to be set by the clinician include:

a) Baseline infusion rate.

b) Maximum infusion rate.

c) Rate step-up amount achieved with each button push.

d) Duration of stepped-up infusion rate.

e) Lock-out interval before pump again responds to button.

f) Physiologic parameters which turn off infusion.

The lock-out interval should be set to reflect the time of onset of the clinical effect of a medication. For remifentanil, the time to onset of effect is about 5–10 minutes. If there is significant variation from this normal range in a given patient, the lock-out interval should be adjusted accordingly.

Figure 7:
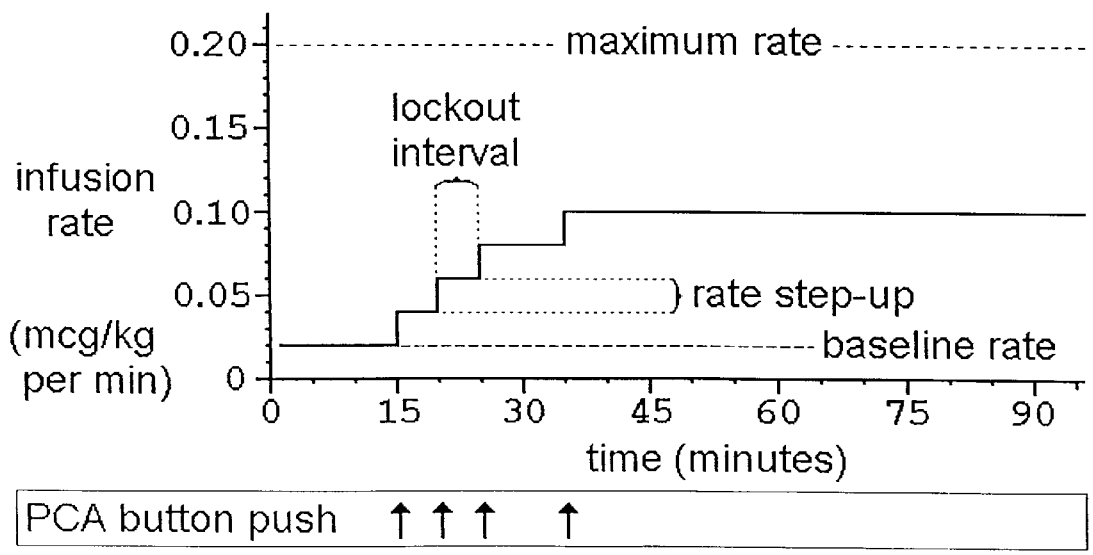
FIGS. 7, 8 and 9 are infusion rate/time graphs.

If pain is only intermittent and long intervals without pain exist, the baseline infusion rate may be set to zero. Otherwise the lowest effective infusion rate that controls a patient's background pain and does not cause side effects should be set. The device can be used to determine the lowest effective infusion rate as follows: (1) Test the patient's response during a period without significant exacerbations above the background pain level. (2) Start with a low initial baseline infusion rate and step-up amount. (3) Set the duration of the stepped up infusion rate very high so that the pump will not step down during this test period. (See FIG. 7.) Allow the patient to increase the infusion rate using the PCA button. Once a patient's background pain is controlled without side-effects, the effective baseline infusion rate has been determined. Patients should always be observed in an appropriate clinical setting while any new opioid medication regimen is being assessed.

The maximum infusion rate should be set at a level somewhat lower than the clinician believes would cause unmanageable or potentially harmful side effects. This level may be increased if a patient develops tolerance or has demonstrated low opioid sensitivity. For opioid naive patients 0.2 mcg/kg/min would be an appropriate initial maximum until their opioid sensitivity is assessed.

Figure 8:
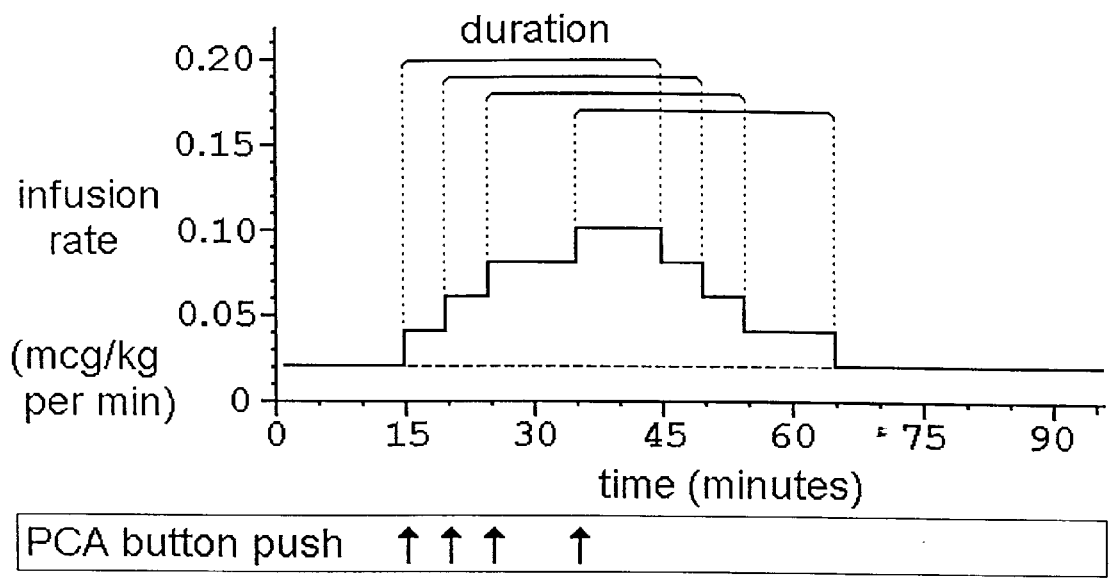

The rate step-up amount should be set low initially while a patient's opioid requirement is being assessed, e.g., 0.025 mcg/kg/min or less. The patient can achieve greater increases in the infusion rate by repeated button pushes. (See FIG. 8.) If a patient is tolerant to opioids or has demonstrated low opioid sensitivity, higher rate step-up amounts may be used.

The duration of an infusion rate step-up should be set to correspond to the anticipated duration of pain exacerbations. The shortest period of exacerbation should be used since the patient can accommodate longer periods, if necessary, by repeated button pushes. (See FIG. 9.)

If the duration of an infusion rate step-up is set to less than the lock-out interval, the patient will be unable to increase the infusion rate by more than one step-up amount.

The physiologic parameters which will discontinue the infusion and trigger an audible alarm should be set according to the patient's normal values. These parameters may include a combination of any of the following: respiratory rate, respiratory depth, hemoglobin oxygen saturation, and patient movement.

In generation, the following practical considerations should be bore in mind, (1) If the baseline infusion controls the pain without significant use of the PCA function, then the patient does not need a short acting intravenous agent. A longer acting agent and possibly another route of administration may be used.

(2) If the pain is unrelieved despite unmanageable side-effects, including sedation or respiratory depression, then the pain is not opioid responsive and this form of therapy should be discontinued.

(3) If the pain is well controlled with the use of step-ups but not at baseline, increase the baseline infusion rate.

(4) If the background pain is well controlled at the baseline infusion rate but side-effects occur, decrease the baseline infusion rate or treat the side-effects if possible.

(5) If there is good effect with use of step-ups for some exacerbations but not others, increase the maximum infusion rate or duration (which ever is limiting use of further step-ups) and/or increase the step-up amount.

Figure 9:
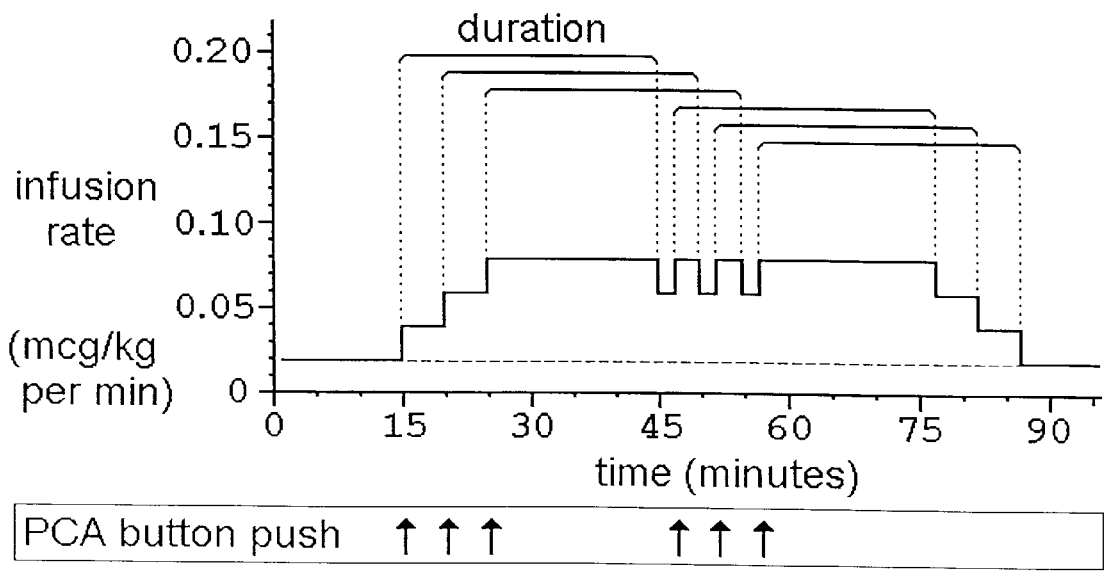

(6) If there is good pain control with use of step-ups but exacerbations consistently outlast the duration of the step-ups (as shown in FIG. 9), increase the duration.

(7) If multiple step-ups are required to treat every exacerbation, increase the step-up amount.

(8) If side-effects are occurring with a single step-up but not at baseline, decrease the step-up amount.

It will be seen from the above that, according to the present invention, there is provided a pump for supplying controlled analgesia, which pump has means for increasing the infusion flow rate of the analgesic in response to a command given by the patient receiving the analgesia, there also being means which provide a lock-out interval during which time actuation of the pump by the patient produces no further incremental increase in flow rate of the analgesic.

Also, the present invention provides a method which carries out the function described above.

It will be understood that the above description of the present invention is susceptible to various modifications, changes and adaptations, and the same are intended to be comprehended within the meaning and range of the equivalents of the appended claims.

What is claimed is:

1. A pump for supplying patient controlled analgesia, said pump comprising means for increasing the infusion flow rate of the analgesic in response to a single command given by the patient receiving the analgesia, and means for providing a lock-out interval during which time actuation of the pump by the patient produces no further incremental increases in the flow rate of the analgesic.

2. A pump as defined in claim 1, further comprising means for setting the infusion rate to a maximum.

3. A pump as defined in claim 1, further comprising means for allowing the patient to decrease the base infusion rate if early symptoms of opioid toxicity occur.

4. A pump as defined in claim 1, further comprising feedback means regarding sedation or respiratory depression that may indicate profound opioid overdose and for triggering discontinuation of the infusion until the patient again commands an increase in the infusion rate.

5. A pump as defined in claim 1, further comprising audible alarm means for arousing the patient in the event of an overdose causing sedation or respiratory depression.

6. A method for supplying analgesia to a patient, comprising the step of increasing the infusion flow rate of the analgesic in response to a single command given by the patient receiving the analgesia, and providing a lock-out interval during which time any further command by the patient produces no further incremental increase in the flow rate of the analgesic.

7. A method as defined in claim 6, wherein the infusion flow rate of the analgesic is increased for a predetermined period of time and is the reduced.

8. A pump for supplying patient controlled analgesia, said pump comprising means for increasing the infusion flow rate of the analgesic in response to a command given by the patient receiving the analgesia; means for providing a lock-out interval during which time actuation of the pump by the patient produces no further incremental increase in the flow rate of the analgesic; and means for allowing the patient to decrease the base infusion rate if early symptoms of opioid toxicity occur.

* * * * *